United States Patent [19]

Samans et al.

[11] 3,998,854
[45] Dec. 21, 1976

[54] TRITHIOPHOSPHITE STABILIZED MALEIC ANHYDRIDE

[75] Inventors: Cecelia Samans, Chicago; Martin R. Spatz, Lisle, both of Ill.

[73] Assignee: Standard Oil Company, Chicago, Ill.

[22] Filed: Aug. 7, 1975

[21] Appl. No.: 602,681

[52] U.S. Cl. ................ 260/346.8 M; 260/346.8 R
[51] Int. Cl.$^2$ ........................................ C07D 307/60
[58] Field of Search ................................ 260/346.8

[56] References Cited
UNITED STATES PATENTS

| | | | |
|---|---|---|---|
| 2,598,634 | 5/1952 | Dazzi | 260/346.8 R |
| 3,205,269 | 9/1965 | Friedman | 260/346.1 R |
| 3,657,397 | 4/1972 | Brannen | 260/346.8 R |
| 3,816,475 | 6/1974 | Wehrman | 260/346.8 M |

*Primary Examiner*—Natalie Trousof
*Assistant Examiner*—R. W. Ramsuer
*Attorney, Agent, or Firm*—William H. Magidson; Arthur G. Gilkes; William T. McClain

[57] ABSTRACT

This invention relates to the heat stabilization of maleic anhydride with trithiophosphites. More particularly, this invention relates to the stabilization of maleic anhydride with trialkyl trithiophosphites.

5 Claims, No Drawings

TRITHIOPHOSPHITE STABILIZED MALEIC ANHYDRIDE

The literature is replete with patents directed to the stabilization of maleic anhydride since maleic anhydride is heat and light sensitive, i.e. it yellows with time and temperature. For the most part, the extent of yellowing depends on the quality of the maleic anhydride as well as the conditions of storage. While the mechanism and cause of the yellowing is not known, this yellowing has been blamed on parts per million level of impurities (reaction and/or processing contaminants and/or by-products) which may react themselves to give yellow impurities or catalyze the degradation of the maleic anhydride.

Normally, commercial maleic anhydride must pass two molten color specifications. The initial color of the maleic anhydride melt must be below a certain accepted value and the maleic anhydride melt must be heat stable for 2 hours at 140° C. Since maleic anhydride is sold in solid form, as briquettes, tablets or pastilles and in the molten form at around 60° C, the maleic anhydride must pass these color specifications, not only after manufacture, but also after extended storage and transportation at 60° C. Further, since chemical additives themselves are incapable of improving off color maleic anhydride, maleic anhydride being stabilized must be of reasonably high quality.

The literature in many cases indicates contradictory results with the same stabilizers. The reason for this is not understood at this time but may be related to the history or method of producing the particular maleic anhydride since maleic anhydride can be produced by oxidation of benzene, saturated and unsaturated $C_4$ hydrocarbons (e.g. butane or butene) or as a by-product of naphthalene oxidation to phthalic anhydride. For example, while Halcon U.S. Pat. No. 3,586,703 indicates that sodium iodide is ineffective, Monsanto British specification No. 1,331,853 discloses the stabilization of maleic anhydride with halogen compounds broadly and illustrates the effectiveness of sodium iodide as a stabilizer for maleic anhydride, (both of these references are incorporated by reference). Our own studies seem to confirm the conclusions of the Halcon Patent. As indicated above, the reason for these discrepancies is unclear and may be related to the method of producing the maleic anhydride, etc.

The general object of this invention is to provide a new class of heat stabilizers for maleic anhydride. Other objects appear hereinafter.

We have now found that maleic anhydride having an initial APHA (American Public Health Association Units in accordance with ASTM D1209-69 platinum-cobalt scale) of at least 10 and 2 hour APHA of at least 50, as determined after being held at 140° C., can be heat stabilized with trithiophosphites. If either the initial APHA is less than 10 or the 2 hour APHA is less than 50, the trithiophosphite does not act as a stabilizer but instead catalyzes the heat degradation of the maleic anhydride. For the purposes of this invention, the term "heat stabilized" or "heat stable" are used to indicate that other things being equal, the maleic anhydride containing trithiophosphite has a lower APHA after being held at 140° C. for 2 or more hours than maleic anhydride containing no stabilizer. The trithiophosphites useful in this invention include any trithiophosphite compounds capable of providing the aforesaid improvement.

The trithiophosphites useful in this invention can be represented by the structure

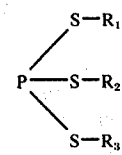

wherein $R_1$, $R_2$ and $R_3$ are independently hydrocarbon groups of from 1 to 25 carbon atoms, such as alkyl groups of 1 to 24 carbon atoms (methyl, ethyl, isopropyl, propyl, butyl, amyl, octyl, 2-ethylhexyl, lauryl, stearyl, tetracosyl, etc.); aryl groups of 6 to 24 carbon atoms (phenyl, naphthyl, toluyl, p-octadecylphenyl, etc.); aralkyl groups containing 7 to 25 carbon atoms (benzyl, p-octadecylbenzyl, etc.); alkenyl groups containing 8 to 24 carbon atoms (oleyl, etc.) etc.

Suitable trithiophosphites include trimethyl trithiophosphite, triethyl trithiophosphite, tripropyl trithiophosphite, triisopropyl trithiophosphite, triamyl trithiophosphite, trihexyl trithiophosphite, tri-2-ethylhexyl trithiophosphite, trioctyl trithiophosphite, trilauryl trithiophosphite, trioleyl trithiophosphite, trihexadecyl trithiophosphite, tristearyl trithiophosphite, tritetracosyl trithiophosphite, triphenyl trithiophosphite, tricresyl trithiophosphite, tribenzyl trithiophosphite, trioctadecylphenyl trithiophosphite, diethyl phenyl trithiophosphite, dilauryl benzyl trithiophosphite, etc. Of these, trialkyl trithiophosphites and particularly the commercially available trilauryl trithiophosphite are preferred. The latter compound which melts at 20° C can be added conveniently to molten maleic anhydride and obtain uniform distribution of the stabilizer at relatively low concentrations.

The trithiophosphites can be used in a stabilizing concentration of about 1 to 2,000 ppm based on the concentration of maleic anhydride. Generally the preferred alkyl trithiophosphites can be utilized in a concentration of about 5 to 200 ppm based on the weight of maleic anhydride. However, larger concentration can be added without degrading the maleic anhydride.

The maleic anhydride utilized in this invention can be produced by any process suitable for the production of maleic anhydride. However, we prefer to use maleic anhydride produced by the oxidation of butane, such as that described in Boghosian U.S. Pat. No. 3,862,146, which is incorporated by reference. In any case, the maleic anhydride should be relatively pure prior to the addition of the stabilizer. Generally, the stabilizer can be added to molten maleic anhydride shortly after the maleic anhydride is distilled from most of its impurities and by-products formed in the oxidation of the particular organic precursor.

The stabilizer can be added to the maleic anhydride neat or in a diluted form. On a commercial basis dilution of the preferred liquid trilauryl trithiophosphite is not necessary. However, if desired, the trithiophosphites can be dissolved in an aromatic hydrocarbon, such as ortho-xylene, para-xylene, meta-xylene, toluene, etc. In the case of solid trithiohosphites, it is generally best to dissolve the stabilizer in an appropriate solvent in order to get uniform distribution of the stabilizer in the maleic anhydride.

The following examples are merely illustrative and should not be construed as limiting the scope of the invention.

EXAMPLE I

After 60 grams of solid maleic anhydride produced by the method of U.S. Pat. No. 3,862,146 was placed in a 50 milliliter/tall-form Nesslerimeter tube, 100 ppm of stabilizer (0.0060 grams neat) was added to the maleic anhydride at room temperature. The maleic anhydride in the Nesslerimeter test tube was melted rapidly in a 140° C tube-block-heater and the mixture blended. Excess maleic anhydride melt was removed leaving a constant 8 inch high liquid level. Immediately thereafter the initial molten color was measured by visual comparison with standard APHA solutions in Nesslerimeter tubes according to ASTM D1209-69 (platinum-cobalt scale). After reading, the tube was placed in the 140° C heater and capped with a 10-milliliter beaker to prevent contamination and the tube heater was covered with a 100 × 190 millimeter crystallization dish. The heat stable colors were read after 2, 4 and 24 hours. The results are set forth below in Table I. Multiple numbers in the Table indicates the range of colors measured for repeat tests.

Table I

| Stabilizer | Molten Color APHA Hours at 140° C | | | |
|---|---|---|---|---|
| | Initial | 2 | 4 | 24 |
| None | 0/10 | 150/200 | 250/350 | >1500 |
| Trilauryl trithiophosphite | 10 | 40 | 45 | 100 |
| Trihexadecyl trithiophosphite | 15 | 45 | 50 | 90 |

The above data indicates that trithiophosphites are effective heat stabilizers of maleic anhydride.

EXAMPLE II

Example I was repeated using a commercially available unstabilized maleic anhydride, which is produced in Spain by the oxidation of benzene, and either 50 or 100 ppm trilauryl trithiophosphite. The results are set forth below in Table II:

Table II

| Stabilizer | Concentration | Molten Color APHA Hours at 140° C | | | |
|---|---|---|---|---|---|
| | | Initial | 2 | 4 | 24 |
| None | | 35/50 | 125/1400 | 250/>1500 | >1500 |
| Present | 50 ppm | 45 | 60 | 80 | 400 |
| Present | 100 ppm | 40 | 60 | 80 | 250 |

We claim:
1. A composition comprising maleic anhydride and a heat stabilizing concentration of trithiophosphite having the structure

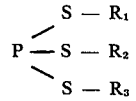

wherein $R_1$, $R_2$, and $R_3$ are independently alkyl groups of 1 to 24 atoms, aryl groups of 6–24 carbon atoms, aralkyl groups containing 7 to 25 carbon atoms and alkenyl groups containing 8 to 24 carbon atoms.
2. The composition of claim 1 where said trithiophosphite is a trialkyl trithiophosphite.
3. The composition of claim 2, wherein said trithiophosphite is present in a concentration of 1 to 2000 ppm based on the concentration of maleic anhydride.
4. The composition of claim 3 wherein said trithiophosphite comprises trilauryl trithiophosphite.
5. The composition of claim 3, wherein said trithiophosphite comprises trihexadecyl trithiophosphite.

* * * * *